United States Patent
Jain et al.

(10) Patent No.: US 11,911,383 B2
(45) Date of Patent: Feb. 27, 2024

(54) ORAL SOLUTION FORMULATION

(71) Applicant: Pfizer Inc., New York, NY (US)

(72) Inventors: Ashwinkumar Jain, East Lyme, CT (US); Weili Yu, Pawcatuck, CT (US)

(73) Assignee: Pfizer Inc., New York, NY (US)

( * ) Notice: Subject to any disclaimer, the term of this patent is extended or adjusted under 35 U.S.C. 154(b) by 443 days.

(21) Appl. No.: 17/055,102

(22) PCT Filed: May 3, 2019

(86) PCT No.: PCT/IB2019/053650
§ 371 (c)(1),
(2) Date: Nov. 12, 2020

(87) PCT Pub. No.: WO2019/220253
PCT Pub. Date: Nov. 21, 2019

(65) Prior Publication Data
US 2021/0205309 A1    Jul. 8, 2021

Related U.S. Application Data

(60) Provisional application No. 62/835,278, filed on Apr. 17, 2019, provisional application No. 62/671,208, filed on May 14, 2018.

(51) Int. Cl.
| | |
|---|---|
| *A61K 31/519* | (2006.01) |
| *A61K 9/00* | (2006.01) |
| *A61K 9/08* | (2006.01) |
| *A61K 47/14* | (2017.01) |
| *A61K 47/26* | (2006.01) |

(52) U.S. Cl.
CPC .......... *A61K 31/519* (2013.01); *A61K 9/0053* (2013.01); *A61K 9/08* (2013.01); *A61K 47/14* (2013.01); *A61K 47/26* (2013.01)

(58) Field of Classification Search
CPC ...... A61K 31/519; A61K 9/0053; A61K 9/08; A61K 47/14; A61K 47/26
See application file for complete search history.

(56) References Cited

U.S. PATENT DOCUMENTS

| | | |
|---|---|---|
| 6,936,612 B2 | 9/2005 | Barvian et al. |
| 7,345,171 B2 | 3/2008 | Beylin et al. |
| 7,456,168 B2 | 11/2008 | Barvian et al. |
| 7,781,583 B2 | 8/2010 | Erdman et al. |
| 7,863,278 B2 | 1/2011 | Beylin et al. |
| RE47,739 E | 11/2019 | Barvian et al. |
| 10,723,730 B2 | 7/2020 | Chekal et al. |
| 2017/0281631 A1 | 10/2017 | Wang et al. |
| 2018/0371021 A1* | 12/2018 | Aivado ............... A61P 35/00 |
| 2020/0054560 A1 | 2/2020 | Zhang et al. |

FOREIGN PATENT DOCUMENTS

| | | |
|---|---|---|
| CN | 104887641 | 12/2017 |
| JP | 2012-526850 A | 11/2012 |
| JP | 2013-545758 A | 12/2013 |
| WO | 2003062236 | 7/2003 |
| WO | 2005005426 | 1/2005 |
| WO | 2008032157 | 3/2008 |
| WO | 2010132725 A2 | 11/2010 |
| WO | 2012068381 A2 | 5/2012 |
| WO | 2014128588 | 8/2014 |
| WO | 2016156070 | 10/2016 |
| WO | 2016193860 | 12/2016 |
| WO | 2018039324 A1 | 3/2018 |
| WO | 2018191950 | 10/2018 |

OTHER PUBLICATIONS

Schiele et al., Eur J Pharmacol (2013) 69:937-948 (Year: 2013).*
Ansel's Pharmaceutical Dosage Forms and Drug Delivery Systems, 10th Ed (2014), pp. 395-444 (Year: 2014).*
Handbook of Pharmaceutical Excipients, 6th Ed, 2009, pp. 587-590, 627-629, 701-703, 786-789. (Year: 2009).*
International Search Report for PCT/IB2019/053650, dated Sep. 2, 2019.
Written Opinion of the International Searching Authority for PCT/IB2019/053650, dated Nov. 21, 2019.
U.S. Appl. No. 15/578,410, filed Nov. 11, 2017.

* cited by examiner

*Primary Examiner* — San Ming R Hu
(74) *Attorney, Agent, or Firm* — Christian M. Smolizza

(57) ABSTRACT

The present invention relates to an oral solution formulation or an oral powder for constitution comprising 6-acetyl-8-cyclopentyl-5-methyl-2-(5-piperazin-1-yl-pyridin-2-ylamino)-8H-pyrido[2,3-d]pyrimidin-7-one, or a lactate or malate salt thereof, and a buffer system comprising lactic acid or malic acid.

18 Claims, No Drawings

ORAL SOLUTION FORMULATION

CROSS-REFERENCE TO RELATED APPLICATIONS

This Application is the national stage filing under 35 U.S.C. 371 of Patent Cooperation Treaty Patent Application No. PCT/162019/053650, filed May 3, 2019, which claims the benefit of priority from U.S. Provisional Application No. 62/835,278 filed Apr. 17, 2019, and U.S. Provisional Application No. 62/671,208 filed May 14, 2018, the contents of each of which are hereby incorporated by reference in their entirety.

BACKGROUND OF THE INVENTION

Field of the Invention

The present invention relates to oral solution formulations comprising 6-acetyl-8-cyclopentyl-5-methyl-2-(5-piperazin-1-yl-pyridin-2-ylamino)-8H-pyrido[2,3-d]pyrimidin-7-one (hereinafter palbociclib), or a lactate or malate salt thereof, a pharmaceutically acceptable solvent, and a buffer system suitable to allow drug stability and preservation.

Description of Related Art

Palbociclib is a potent and selective inhibitor of CDK4 and CDK6, having the structure:

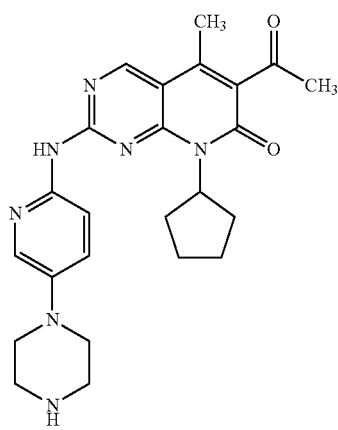 [SMILES: CC(=O)c1c(C)c2cnc(Nc3ccc(N4CCNCC4)cn3)nc2n(C2CCCC2)c1=O]

Palbociclib is described in WHO Drug Information, Vol. 27, No. 2, page 172 (2013). Palbociclib and pharmaceutically acceptable salts thereof are disclosed in International Publication No. WO 2003/062236 and U.S. Pat. Nos. 6,936,612, 7,208,489 and 7,456,168; International Publication No. WO 2005/005426 and U.S. Pat. Nos. 7,345,171 and 7,863,278; International Publication No. WO 2008/032157 and U.S. Pat. No. 7,781,583; and International Publication No. WO 2014/128588. Solid formulations of palbociclib are disclosed in International Publication No. WO 2016/193860. The contents of each of the foregoing references are incorporated herein by reference in their entirety.

There is a need to develop a palatable, pharmaceutically acceptable oral solution formulation of palbociclib that is suitable for use in pediatric subjects, in subjects having a nasogastric (NG) tube, or in subjects having difficulty swallowing solid dosage forms, such as tablets or capsules. Such oral solution formulations may have advantageous biopharmaceutical properties, e.g., with respect to food effects or effects on co-administration with proton-pump inhibitors (PPIs).

BRIEF SUMMARY OF THE INVENTION

The present invention provides an oral solution formulation comprising palbociclib, or a lactate or malate salt thereof, a pharmaceutically acceptable solvent and a buffer system comprising lactic acid or malic acid, or a salt of lactic or malic acid. In frequent embodiments, the solvent comprises water and optionally further comprises a pharmaceutically acceptable co-solvent.

In one aspect, the invention provides an oral solution formulation comprising palbociclib, or a lactate or malate salt thereof, and a buffer system comprising lactic acid or malic acid. In some such embodiments, palbociclib is in the form of a free base. In other such embodiments, palbociclib is in the form of the lactate or malate salt. In one aspect, the invention provides an oral solution formulation comprising palbociclib, or a lactate salt thereof, and a buffer system comprising lactic acid, or a salt of lactic acid. In some such embodiments, palbociclib is in the form of a free base. In other such embodiments, palbociclib is in the form of the lactate salt.

In another aspect, the invention provides an oral solution formulation comprising palbociclib, or a malate salt thereof, and a buffer system comprising malic acid, or a salt of malic acid. In some such embodiments, palbociclib is in the form of a free base. In other such embodiments, palbociclib is in the form of the malate salt.

Such oral solution formulations may be provided ready-to-use by a patient in need thereof. Alternatively, such oral solution formulations may be prepared from an oral powder for constitution (OPC) at the time of use. Such OPC dosage forms can be formulated and reconstituted via any known procedure. In some embodiments, the dosage form is a powder in bottle that is reconstituted by adding water and agitating to deliver the desired dose.

DETAILED DESCRIPTION OF THE INVENTION

The present invention may be understood more readily by reference to the following detailed description of the preferred embodiments of the invention and the Examples included herein. The terminology used herein is for the purpose of describing specific embodiments only. It is further to be understood that unless specifically defined herein, the terminology used herein is to be given its traditional meaning as known in the relevant art.

As used herein, the singular form "a", "an", and "the" include plural references unless indicated otherwise. For example, "a" substituent includes one or more substituents.

As used herein, the term "about" means having a value falling within an accepted standard of error of the mean when considered by one of ordinary skill in the art. Frequently, the term "about" refers to ±20%, preferably ±10%, and more preferably ±5% of the value or range to which it refers.

The invention described herein may be practiced in the absence of any element(s) not specifically disclosed herein. Thus, for example, in each instance herein any of the terms "comprising", "consisting essentially of", and "consisting of" may be replaced with either of the other two terms.

The present invention provides an oral solution formulation comprising palbociclib, or a lactate or malate salt thereof, a pharmaceutically acceptable solvent, and a buffer system comprising lactic acid or malic acid.

The oral solution formulations of the invention may be formulated with any pharmaceutically acceptable solvent suitable for oral administration. In preferred embodiments, the pharmaceutically acceptable solvent comprises water, and such oral solution formulations may be referred to herein as "oral aqueous solution formulations." In some embodiments, the pharmaceutically acceptable solvent comprises water and optionally further comprises a pharmaceutically acceptable co-solvent, e.g., propylene glycol, polyethylene glycol 400 (PEG 400), glycerin, ethanol, or combinations thereof.

The solubility of palbociclib was investigated in aqueous buffer systems within a pH range from 2.0 to 8.4 and at temperatures from 25° C. to 40° C. Results of the solubility experiments are provided in Table 1. Surprisingly, it was found that palbociclib had significantly enhanced solubility in aqueous buffer systems of lactic acid and malic acid, with minimal degradation. Therefore, either lactic acid or malic acid was included in the buffer systems for the oral solution formulations described herein. Such buffer systems are stable and compatible with the active pharmaceutical ingredient (API) and further excipients, at a pH range of from about 3.0 to about 4.5, preferably at a pH range of from about 3.6 to about 4.0, and more preferably at a pH of about 3.8

In one aspect, the invention provides an oral aqueous solution formulation comprising palbociclib, or a lactate or malate salt thereof, and a buffer system comprising lactic acid or malic acid. In some such embodiments, palbociclib is in the form of a free base. In other such embodiments, palbociclib is in the form of the lactate salt and the buffer comprises lactic acid. In other such embodiments, palbociclib is in the form of the malate salt and the buffer comprises malic acid. In some such embodiments, the solution comprises one or more taste enhancing or taste masking agents.

In one aspect, the invention provides an oral aqueous solution formulation comprising palbociclib, or a lactate salt thereof, and a buffer system comprising lactic acid. In some such embodiments, palbociclib is in the form of a free base. In other such embodiments, palbociclib is in the form of the lactate salt. In some such embodiments, the solution comprises one or more taste enhancing or taste masking agents.

In another aspect, the invention provides an oral aqueous solution formulation comprising palbociclib, or a malate salt thereof, and a buffer system comprising malic acid. In some such embodiments, palbociclib is in the form of a free base. In other such embodiments, palbociclib is in the form of the malate salt. In some such embodiments, the solution comprises one or more taste enhancing or taste masking agents.

In some embodiments, the oral aqueous solution formulation comprises palbociclib, or a lactate or malate salt thereof, at a solution concentration of from about 10 mg/mL to about 50 mg/mL, preferably at a solution concentration of from about 12.5 mg/mL to about 25 mg/mL, wherein the concentration refers to the free base form of palbociclib, or is calculated as the free base equivalent for the palbociclib lactate or malate salt forms. In some embodiments, the oral aqueous solution formulation comprises palbociclib, or a lactate or malate salt thereof, at a solution concentration of up to about 40.0 mg/mL, about 35.0 mg/mL about 30.0 mg/mL, about 25.0 mg/mL, about 20.0 mg/mL about 15.0 mg/mL, about 12.5 mg/mL or about 10.0 mg/mL.

In some embodiments, the oral aqueous solution formulation comprises palbociclib at a solution concentration of about 25.0 mg/mL. In some embodiments, the oral aqueous solution comprises palbociclib at a solution concentration of about 12.5 mg/mL. In some embodiments, the oral aqueous solution comprises palbociclib at a solution concentration of about 10.0 mg/mL.

In some embodiments, the oral aqueous solution comprises palbociclib, or a lactate salt thereof, at a solution concentration of about 25.0 mg/mL. In some embodiments, the oral aqueous solution comprises palbociclib, or a lactate salt thereof, at a solution concentration of about 12.5 mg/mL. In some such embodiments, the buffer system comprises lactic acid.

In some such embodiments, the oral aqueous solution comprises palbociclib, or a malate salt thereof, at a solution concentration of about 12.5 mg/mL. In some such embodiments, the oral aqueous solution comprises palbociclib, or a malate salt thereof, at a solution concentration of about 10.0 mg/mL. In some such embodiments, the buffer system comprises malic acid.

In some embodiments, the oral aqueous solution comprises palbociclib, or a lactate salt thereof, at a solution concentration of at least 10.0 mg/mL, at least 12.5 mg/mL, at least 15.0 mg/mL, at least 20.0 mg/mL, or at least 25.0 mg/mL. In some such embodiments, the buffer system comprises lactic acid.

In some embodiments, the oral aqueous solution comprises palbociclib, or a malate salt thereof, at a solution concentration of at least 10.0 mg/mL, at least 12.5 mg/mL, or at least 15.0 mg/mL. In some such embodiments, the buffer system comprises malic acid.

The oral aqueous solutions of the present invention include a buffer system comprising lactic acid or malic acid. Such buffer systems are stable and compatible with the API and further excipients.

In some embodiments, the buffer system comprises lactic acid at a concentration of from about 0.05M to about 0.2M. In some embodiments, the buffer system comprises lactic acid at a concentration of about 0.1M. In some embodiments, the buffer system comprises lactic acid at a concentration of about 0.2M. In some embodiments, the buffer system comprises lactic acid at a concentration of up to about 0.2M. DL-lactic acid, D-lactic acid or L-lactic acid, or mixtures thereof, may be used in the oral solutions of the invention. In frequent embodiments, the buffer system comprises DL-lactic acid.

In some embodiments, the buffer system comprises malic acid at a concentration of from about 0.1M to about 0.2M. In some embodiments, the buffer system comprises malic acid at a concentration of about 0.1M. In some embodiments, the buffer system comprises malic acid at a concentration of about 0.2M. DL-malic acid, D-malic acid or L-malic acid, or mixtures thereof, may be used in the oral solutions of the invention. In some embodiments, the buffer system comprises L-malic acid.

The oral aqueous solutions of the present inventions are buffered to a pH range that provides a stable formulation wherein the components remain in solution at a unit dose volume that is suitable for oral administration. Preferably, the dosage volume is from about 5 mL to about 15 mL. More preferably, the dosage volume is from about 5 mL to about 10 mL. For a standard adult dose of 125 mg API, a concentration of 12.5 mg/mL corresponds to a 10 mL dosage volume, while a concentration of 25.0 mg/mL corresponds to a 5 mL dosage volume.

In some embodiments; trace amounts of dilute acid (e.g., 10% aq. hydrochloric acid) are used to adjust the pH range of the buffer system to fall within the targeted pH range.

In some embodiments, the oral aqueous solution has a pH of from about 3.0 to about 4.5. In some embodiments, the oral aqueous solution has a pH of from about 3.5 to about 4.3. In frequent embodiments, the oral aqueous solution has a pH of from about 3.6 to about 4.0. In some such embodiments, the oral aqueous solution has a pH of about 3.8. Increased degradation was observed at pH values below about pH 3.5. Some precipitation of the API was observed at pH values above about 4.3.

In some embodiments, the oral aqueous solution further comprises one or more taste-enhancing or taste-masking agents, such as sweeteners, flavorants, or mouth feel modifying excipients. Such excipients may be used to mask bitterness and/or after-taste of the API, or to modify mouth feel to enhance palatability.

In frequent embodiments, the oral solution comprises one or more pharmaceutically acceptable sweeteners. In some embodiments, the oral solution comprises one or more pharmaceutically acceptable sweeteners selected from the group consisting of xylitol, sucralose, acesulfame potassium, saccharin, sodium saccharin, calcium saccharin, aspartame, neotame, advantame, stevioside, sucrose, fructose, glucose, dextrose, maltitol, sorbitol and mannitol, or mixtures thereof. Intense sweeteners, e.g., sucralose, are typically included in a concentration range of from about 0.05 mg/mL to about 15.0 mg/mL. Bulk sweeteners, e.g., xylitol, can be used in larger quantities, for example from about 100.0 mg/mL to about 350.0 mg/mL, or from about 50.0 mg/mL to about 500.0 mg/mL.

In some embodiments, the oral solution comprises xylitol at a solution concentration of about 100.0 mg/mL to about 350.0 mg/mL. In some such embodiments, the oral solution comprises xylitol at a solution concentration of about 320.0 mg/mL. In other such embodiments, the oral solution comprises xylitol at a solution concentration of about 100.0 mg/mL.

In some embodiments, the oral solution comprises sucralose at a solution concentration of about 1.0 mg/mL to about 10.0 mg/mL. In some such embodiments, the oral solution comprises sucralose at a solution concentration of about 8.0 mg/mL. In other such embodiments, the oral solution comprises sucralose at a solution concentration of about 1.0 mg/mL.

In some embodiments, the oral aqueous solution comprises one or more pharmaceutically acceptable sweeteners selected from xylitol at a solution concentration from about 100.0 mg/mL to about 350.0 mg/mL and sucralose at a solution concentration from about 1.0 mg/mL to about 10.0 mg/mL, or mixtures thereof.

In one preferred embodiment, the oral solution comprises xylitol at a solution concentration of about 320.0 mg/mL and sucralose at a solution concentration of about 8.0 mg/mL. In another preferred embodiment, the oral solution comprises xylitol at a solution concentration of about 100.0 mg/mL and sucralose at a solution concentration of about 1.00 mg/mL.

A variety of different pharmaceutically acceptable flavorants may be included in the formulations of the present invention to mask the bitter flavour of the API. Flavorants include, but are not limited to grape, orange, cherry, strawberry or raspberry flavorants. Flavorants are typically included in a concentration range of from about 0.5 mg/mL to about 10.0 mg/mL and should be completely soluble in the drug formulation. In some embodiments, the flavorant is included at a concentration of from about 1.0 mg/mL to about 5.0 mg/mL. In some embodiments, the flavorant is included at a concentration of from about 1.0 mg/mL to about 3.0 mg/mL.

In some embodiments, the oral aqueous solutions of the invention further comprise one or more pharmaceutically acceptable excipients selected from the group consisting of antimicrobial preservatives, antioxidants, pH adjusting agents, diluents, solubilizing agents, viscosity modifying agents and colorants.

In some embodiments, the oral solution further comprises one or more antimicrobial preservatives. Suitable antimicrobial preservatives include, but are not limited to, benzoic acid or a pharmaceutically acceptable salt thereof, sorbic acid or a pharmaceutically acceptable salt thereof, propionic acid or a pharmaceutically acceptable salt thereof, or a paraben ester or a pharmaceutically acceptable salt thereof. Typically, the preservative is included in a concentration range of from about 0.1 mg/mL to about 2.5 mg/mL, from about 0.1 mg/mL to about 1.5 mg/mL, and sometimes from about 1.0 mg/mL to about 1.5 mg/mL.

In some embodiments, the preservative is sodium benzoate or benzoic acid. In some embodiments, the preservative is sodium benzoate. In some embodiments, the preservative is sorbic acid or potassium sorbate. In some embodiments, the preservative is propionic acid or sodium propionate. In some embodiments, the preservative is methyl, ethyl, or propyl paraben, or a mixture thereof. In some embodiments, the preservative is methyl paraben and sodium benzoate.

In some embodiments, the oral solution comprises sodium benzoate at a concentration of about 0.1 mg/mL to about 1.5 mg/mL. In some such embodiments, the oral solution comprises sodium benzoate at a concentration of about 1.0 mg/mL. In other such embodiments, the oral solution comprises sodium benzoate at a concentration of about 1.5 mg/mL.

In some embodiments, the oral solution further comprises one or more antioxidants. Suitable antioxidants include, but are not limited to, propyl gallate, ascorbic acid and pharmaceutically acceptable salts or esters thereof, butylated hydroxyanisole (BHA), butylated hydroxytoluene (BHT), cystein/cysteinate HCl, dithionite sodium (Na hydrosulfite, Na sulfoxylate), gentisic acid and pharmaceutically acceptable salts thereof, ethylenediaminetetraacelic acid (EDTA) and pharmaceutically acceptable salts thereof (e.g., disodium EDTA), glutamate monosodium, glutathione, methionine, monothioglycerol, $\alpha$-tocopherol and pharmaceutically acceptable salts thereof, thioglycolate sodium, or mixtures thereof.

Antioxidants are typically included at concentration range of from about 0.01 mg/mL to about 5.0 mg/mL. In some embodiments, the solution comprises one or more antioxidants, each at a solution concentration of from about 0.1 mg/mL to about 1.0 mg/mL.

In some embodiments, the oral solution comprises propyl gallate at a concentration of about 0.025 mg/mL to about 1.0 mg/mL. In some embodiments, the oral solution comprises propyl gallate at a concentration of about 0.25 mg/mL to about 1.50 mg/mL. In some embodiments, the oral solution comprises propyl gallate at a concentration of about 0.025 mg/mL to about 2.0 mg/mL. In some such embodiments, the oral solution comprises propyl gallate at a solution concentration of about 0.10 mg/mL. In some such embodiments, the oral solution comprises propyl gallate at a solution concentration of about 0.5 mg/mL. In some such embodiments, the oral solution comprises propyl gallate at a solution concentration of about 1.0 mg/mL.

In some embodiments, the oral solution comprises EDTA or a pharmaceutically acceptable salt thereof, at a concentration of about 0.025 mg/mL to about 1.0 mg/mL. In some embodiments, the oral solution comprises EDTA or a pharmaceutically acceptable salt thereof, at a concentration of about 0.025 mg/mL to about 2.0 mg/mL. In some embodiments, the oral solution comprises EDTA or a pharmaceutically acceptable salt thereof, at a concentration of about 0.25 mg/mL to about 1.50 mg/mL. In some embodiments, the oral solution comprises EDTA or a pharmaceutically acceptable salt thereof, at a solution concentration of about 1.0 mg/mL. In some embodiments, the oral solution comprises EDTA or a pharmaceutically acceptable salt thereof, at a solution concentration of about 0.1 mg/mL. In such embodiments, EDTA is frequently in the form of the disodium salt. In some embodiments, the oral solution comprises disodium EDTA at a solution concentration of about 1.0 mg/mL. In some embodiments, the oral solution comprises disodium EDTA at a solution concentration of about 0.1 mg/mL.

In some embodiments, the oral solution comprises propyl gallate at a concentration of about 0.025 mg/mL to about 1.0 mg/mL and disodium EDTA at a concentration of about 0.025 mg/mL to about 1.0 mg/mL. In some such embodiments, the oral solution comprises propyl gallate at a solution concentration of about 1.0 mg/mL and disodium EDTA at a solution concentration of about 1.0 mg/mL.

In another aspect, the invention provides an oral aqueous solution comprising palbociclib at a solution concentration of about 25.0 mg/mL, lactic acid at a solution concentration of about 0.1M, xylitol at a solution concentration of about 320.0 mg/mL and sucralose at a solution concentration of about 8.0 mg/mL, said solution having a pH of from about 3.6 to about 4.0. In some such embodiments, the solution further comprises: (a) a pharmaceutically acceptable flavorant at a solution concentration from about 1.0 mg/mL to about 3.0 mg/mL; (b) sodium benzoate at a solution concentration of about 1.0 mg/mL; and/or (c) propyl gallate at a solution concentration of about 0.10 mg/mL In another aspect, the invention provides an oral aqueous solution comprising palbociclib at a solution concentration of about 12.5 mg/mL, malic acid at a solution concentration of about 0.2M, xylitol at a solution concentration of about 100.0 mg/mL and sucralose at a solution concentration of about 1.0 mg/mL, said solution having a pH of from about 3.6 to about 4.0. In some such embodiments, the solution further comprises: (a) a pharmaceutically acceptable flavorant at a solution concentration from about 1.0 mg/mL to about 3.0 mg/mL; (b) sodium benzoate at a solution concentration of about 1.5 mg/mL; and/or (c) propyl gallate at a solution concentration of about 1.0 mg/mL The formulations of the present invention may also include other pH adjusting agents in addition to the lactic acid and malic acid buffer systems already described. Other pH adjusting agents include, but are not limited to, citric acid, phosphoric acid, succinic acid, tartaric acid or acetic acid, and salts thereof. Also included are sodium hydroxide, sodium phosphate, sodium chloride, disodium hydrogen phosphate, sodium hydrogen carbonate, monosodium phosphate, monopotassium phosphate, potassium citrate and mixtures thereof. Such pH adjusting agents may be used in a range of from about 0.01% to about 5% by weight.

The formulations of the present invention may include one or more diluents, for example to adjust the formulation thickness or concentration. Diluents can also serve other purposes in the formulations (e.g., as bulk sweeteners, such as xylitol) and may be included in a range of from about 5% to about 80% by weight.

The formulations of the present invention may include one or more solubilizing agents, such as pharmaceutically acceptable glycols, alcohols, ketones, oils, cyclodextrins and the like.

The formulations of the present invention may comprise one or more viscosity modifying agents. Examples of viscosity modifying agents include, but are not limited to, polyvinyl pyrrolidone, hypromellose, polyacrylate and polyacrylate copolymer resins, celluloses and cellulose derivatives, hydroxyalkyl-celluloses, xanthan gum, polyvinyl resins, polyethylene glycol, polyethylene oxide, sorbitol, sucrose, xylitol, dextrose, fructose, maltitol, sugar, sodium alginate and the like. Viscosity modifying agents may be included in a range of from about 0.05% to about 10% by weight.

Optionally, the formulations of the invention may include colorants, which may include pharmaceutically acceptable natural or synthetic dyes.

In another aspect, the invention provides a method of treating a subject in need thereof comprising administering a therapeutically effective amount of an oral solution of the present invention. In some such embodiments, the oral solution is prepared by reconstitution of a powder for constitution formulation of the invention.

In a further aspect, the invention provides a method of treating cancer (e.g., breast cancer, esophageal cancer, or head and neck cancer) by administering to a subject in need thereof a therapeutically effective amount of palbociclib as an oral solution of the present invention. In some such embodiments, the oral solution is prepared by reconstitution of a powder for constitution formulation of the invention. In a further aspect, the invention provides the use of an oral solution formulation of the present invention for the treatment of cancer in a subject in need thereof.

The term "therapeutically effective amount" as used herein refers to that amount of a compound being administered which will relieve to some extent one or more of the symptoms of the disorder being treated.

At a standard adult dose of 125.0 mg palbociclib, it will be understood that a solution concentration of about 25.0 mg/mL corresponds to an oral solution volume of about 5.0 mL per unit dose, while a solution concentration of about 12.5 mg/mL corresponds to an oral solution volume of about 10.0 mL per unit dose. At a dose of 100.0 mg palbociclib, a solution concentration of about 25.0 mg/mL corresponds to an oral solution volume of about 4.0 mL per unit dose, while a solution concentration of about 12.5 mg/mL corresponds to an oral solution volume of about 8.0 mL per unit dose. At a dose of 75.0 mg palbociclib, a solution concentration of about 25.0 mg/mL corresponds to an oral solution volume of about 3.0 mL per unit dose, while a solution concentration of about 12.5 mg/mL corresponds to an oral solution volume of about 6.0 mL per unit dose. At a dose of 25.0 mg palbociclib, a solution concentration of about 25.0 mg/mL corresponds to an oral solution volume of about 1.0 mL per unit dose, while a solution concentration of about 12.5 mg/mL corresponds to an oral solution volume of about 2.0 mL per unit dose.

In another aspect, the invention provides a powder composition for constitution at the time of use as an oral aqueous solution. Such formulations are sometimes referred to as an oral powder for constitution, or "OPC" formulation. OPC formulations can be formulated and reconstituted via any known procedure. In some embodiments, the dosage form is a dry powder that is reconstituted by adding water and agitating.

A powder for constitution formulation may be reconstituted by mixing the powder with a predetermined amount of water to form an oral aqueous solution of palbociclib, or a lactate or malate salt thereof, as further described herein. Such oral powder for constitution compositions may have improved storage stability or shelf life. The concentration of the components of the powder composition of the present invention may be reflected as a theoretical weight (g) or a weight percent (wt. %) based on the total weight of the powder composition.

In some embodiments, the invention provides an oral powder for constitution comprising about 0.1 wt % to about 20.0 wt % palbociclib, or a lactate or malate salt thereof. In some embodiments, the invention provides an oral powder for constitution comprising about 3.0 wt % to about 15.0 wt % palbociclib, or a lactate or malate salt thereof. In other embodiments, the invention provides an oral powder for constitution comprising about 5.0 wt % to about 10.0 wt % palbociclib, or a lactate or malate salt thereof. In still other embodiments, the invention provides an oral powder for constitution comprising about 5.0 wt % to about 10.0 wt % palbociclib Oral powders for constitution can be prepared by combining the components of the mixture and dry blending, e.g., in a bin blender, or via lyophilization of a mixture comprising the components in an appropriate solvent. The powder may be filled in bottles. The powder in bottle may be reconstituted with water to deliver the desired dose.

In some embodiments, the oral powder for constitution comprises one or more taste-enhancing or taste-masking agents, such as sweeteners, flavorants, or mouth feel modifying excipients. In some embodiments, the powder composition comprises one or more sweeteners. In some such embodiments, the sweeteners are selected from the group consisting of xylitol, sucralose, acesulfame potassium, saccharin, sodium saccharin, calcium saccharin, aspartame, neotame, advantame, stevioside, sucrose, fructose, glucose, dextrose, maltitol, sorbitol and mannitol, or mixtures thereof.

In some such embodiments, the sweetener(s) are present in an amount from about 5% to about 90% by weight of the powder composition. Intense sweeteners, e.g., sucralose, may be included in a range of from about 0.25 wt % to about 5.0 wt %, and frequently from about 0.50 wt % to about 3.0 wt %. Bulk sweeteners, e.g., xylitol, can be used in larger quantities, for example from about 25.0 wt % to about 80.0 wt %.

In some embodiments, the powder composition comprises a buffering agent to maintain the composition pH within an acceptable range for stability of the API. Suitable buffering agents as described herein include lactic acid, malic acid, or salts thereof. In certain embodiments, the buffering agent is present in an amount of about 1 wt % to about 20 wt %. In some embodiments, the buffering agent is present in an amount of about 15.0 wt % to about 25 wt %. In some such embodiments, the buffer is malic acid.

The powder composition may further comprise one or more pharmaceutically acceptable excipients selected from the group consisting of antimicrobial preservatives, antioxidants, pH adjusting agents, diluents, solubilizing agents, viscosity modifying agents, flavorants and colorants.

In some embodiments, the powder composition comprises a preservative, such as those described herein for oral aqueous solutions. In some such embodiments, a preservative may be present in the powder composition in an amount of about 0.01 wt % to about 5 wt %.

In some embodiments, the powder composition comprises a flavorant such as those described herein for oral aqueous solutions. In some such embodiments, a flavorant may be present in the powder composition in an amount of about 0.1 wt % to about 5 wt %.

In one aspect, the invention provides an oral powder for constitution comprising from about 5.0 wt % to about 15.0 wt % palbociclib, or a lactate or malate salt thereof. In some embodiments, the oral powder for constitution comprises a buffer system comprising about 15.0 wt % to about 25.0 wt % lactic acid or malic acid.

In one embodiment, the invention provides an oral powder for constitution comprising about 5.0 wt % to about 15.0 wt % palbociclib, or malate salt thereof, and about 15.0 wt % to about 25 wt % malic acid.

In one embodiment, the invention provides an oral powder for constitution comprising about 8.0 wt % to about 1.0 wt % palbociclib, or a malate salt thereof, and about 18.0 wt % to about 20 wt % malic acid.

In some embodiments, the oral powder for constitution further comprises one or more pharmaceutically acceptable excipients selected from the group consisting of buffering agents, pH adjusting agents, sweeteners, flavorants, preservatives, antioxidants, diluents, solubilizing agents, viscosity modifying agents and colorants.

In some such embodiments, the oral powder for constitution further comprises: (a) one or more preservatives selected from benzoic acid and sodium benzoate, each from about 1.0 wt % to about 1.5 wt %; (b) one or more sweeteners selected from xylitol at from about 50.0 wt % to about 75.0 wt % and sucralose at from about 0.5 wt % to about 1.0 wt %; and/or (c) an antioxidant, wherein the antioxidant is EDTA at from about 0.01 wt % to about 1.0 wt %.

In a further aspect, the invention provides a method of preparing an oral aqueous solution comprising palbociclib, or a lactate or malate salt thereof, comprising the step of dissolving the powder for constitution as described herein in a pharmaceutically acceptable solvent comprising water and optionally comprising a pharmaceutically acceptable co-solvent. In some embodiments, palbociclib, or a lactate or malate salt thereof, is present in the oral aqueous solution formed by reconstitution o the powder for constitution formulations herein at a solution concentration of up to about 40.0 mg/mL.

In some embodiments, palbociclib, or a malate salt thereof, is present in the oral aqueous solution formed by reconstitution o the powder for constitution formulations herein at a solution concentration of about 15.0 mg/mL, about 12.5 mg/mL or about 10.0 mg/mL. In some embodiments, palbociclib, or a lactate salt thereof, is present in the oral aqueous solution formed by reconstitution o the powder for constitution formulations herein at a solution concentration of about 25.0 mg/mL or about 12.5 mg/mL.

As used herein, "subject" refers to a human or animal subject. In certain preferred embodiments, the subject is a human. In some embodiments, the subject is a patient afflicted with a disease state. In other embodiments, the subject may be a healthy volunteer. In some embodiments, the subject is a pediatric patient. In other embodiments, the subject has difficulty swallowing an oral dosage form, such as a capsule or tablet. In other embodiments, the subject has a nasogastric (NG) tube.

The term "treating", as used herein, unless otherwise indicated, means reversing, alleviating, inhibiting the progress of, or preventing the disorder or condition to which such term applies, or one or more symptoms of such disorder or condition. The term "treatment", as used herein, unless otherwise indicated, refers to the act of treating as defined immediately above. The term "treating" also includes adjuvant and neo-adjuvant treatment of a subject.

The oral solutions of palbociclib described herein may be administered alone, or in combination with another anti-cancer therapeutic agent, such as a standard of care agent for the type of cancer being treated. In another aspect, the invention provides a method making an oral aqueous solution of palbociclib, or a lactate or malate salt thereof, as further described herein.

The invention will be illustrated in the following non-limiting examples.

EXAMPLES

Example 1

Solubility of Palbociclib in Various Buffers

The solubility of palbociclib (free base) was assessed in various aqueous buffer solutions and mixtures thereof. The buffers were prepared at concentrations ranging from 0.01 M to 0.2 M and at pH values ranging from 2.0 to 8.4. Samples were prepared by weighing and transferring approximately 200 mg of palbociclib to 3-4 mL of the buffer. The solutions were vortexed and placed in a temperature cycle chamber for 8 hours at 25° C., followed by 12 hours at 40° C., then 8 hours at 25° C. The resulting solutions were then analyzed by HPLC to determine the solubility (mg/mL) of palbociclib in the buffer.

Results are provided in Table 1 below. The total degradation (%) includes only new HPLC peaks greater than 0.05%, and peaks exhibiting significant change from levels present in the in-going API. NT=Not tested.

TABLE 1

Solubility of palbociclib (free base) in buffer

| Sample | Buffers | pH | Solubility (mg/mL) | Total Degradation (%) |
|---|---|---|---|---|
| A | 0.2M Citric Acid | 2.02 | 4.0 | 0.52 |
| B | 0.2M Malic Acid | 2.00 | 15.7 | 0.20 |
| C | 0.2M DL Lactic Acid | 2.07 | 45.7 | 0 |
| D | 0.2M Succinic acid | 2.42 | 1.1 | 0.66 |
| E | 0.2M Sodium succinate | 8.38 | 0.004 | 0 |
| F | 0.2M Sodium dihydrogen phosphate dihydrate | 2.01 | 0.65 | 1.27 |
| G | 9.5 mL D + 0.5 mL E | 3.15 | 1.7 | 0.29 |
| H | 9 mL D + 1 mL E | 3.45 | 0.34 | 3.03 |
| I | 8 mL D + 2 mL E | 3.93 | 0.067 | 3.43 |
| J | 5 mL D + 5 mL E | 4.62 | 0.068 | 1.31 |
| K | 5 mL D + 10 mL E | 4.98 | 0.055 | 1.08 |
| L | 5 mL D + 15 mL E | 5.25 | 0.091 | 1.46 |
| M | 0.1M DL Lactic Acid | 2.31 | 36.3 | 0.00 |
| N | 0.05M DL Lactic Acid | 2.46 | 16.2 | 0.00 |
| O | 0.01M DL Lactic Acid | 2.83 | 3.8 | 0.19 |
| P | 0.032M Malic Acid | NT | 0.53 | 1.66 |
| Q | 0.02M Malic Acid | NT | 0.60 | 1.62 |
| R | 0.01M Malic Acid | NT | 0.60 | 1.63 |

In 0.2M DL lactic acid buffer, the solution was still clear upon dissolution of 45.7 mg API, such that the saturated solubility had not yet been reached. At 25 mg/mL of API, the solution concentration is ~56 mmol and lactic acid buffer is at 100 mmol, or about a two-fold excess. The API solubility drops as the concentration of DL-lactic acid decreases from 0.2M to 0.1M, and then again to 0.01M.

Example 2

Oral Solution Formulation Comprising Lactic Acid

Quantities of the formulation components are calculated to provide a final solution concentration of 25.00 mg/mL palbociclib (free base) API.

A clean, suitable vessel was charged with 550 mg/mL Water for Injection, 55% of the total volume required for the batch. The water temperature was maintained at 15-30° C. Propyl gallate (0.1 mg/mL), sodium benzoate (1.00 mg/mL), and sucralose (8.00 mg/mL) were weighed and added to the compounding vessel while continuously mixing. The components were mixed for a minimum of 10 minutes or until completely dissolved. After visually verifying that all the ingredients had completely dissolved, DL-Lactic Acid (purity 88-92%) (10.13 mg/mL; adjusted for purity: Wt of DL lactic acid=100 mM×90.08 (mol. Wt)×1 mL/88.9% (Purity factor)=10.13 mg) was weighed and added to the vessel while continuously mixing to achieve a final buffer concentration of 0.1 M. The palbociclib free base API (25.00 mg/mL) was weighed and added to the vessel while continuously mixing. The API was added slowly over a period of 10 to 15 minutes to avoid clumping. Once the API was completely added to the compounding vessel, the solution was mixed for a minimum of 1 hour or until all the API had dissolved. After visually verifying complete dissolution of the API, Xylitol (320.00 mg/mL) was weighed and added to the vessel while continuously mixing. The Xylitol was added slowly over a period of 10 to 15 minutes to avoid clumping. The solution was mixed for a minimum of 10 minutes or until Xylitol had dissolved. After visually verifying complete dissolution of the Xylitol, Grape Flavor (Firmenich Natural Grape Flavor (534732 T); Ingredients declaration: >50% Propylene Glycol; 10-25% Glycerin; 1-10% Natural Flavors) (3.00 mg/mL) was weighed and added to the vessel while continuously mixing. The solution was mixed for a minimum of 10 minutes. After the Grape flavor has completely mixed, trace HCl (0.005 mg/mL; 5 mL of 10% HCl per 1 L solution) was weighed and added to the vessel while continuously mixing, as needed to adjust pH. The solution was mixed for a minimum of 10 minutes. The pH of the solution was measured to confirm that the pH was between 3.6 and 4.0 (target pH 3.8). While continuously mixing, the remaining Water for Injection (q.s. to 1 mL) was added to the compounding vessel and the solution was mixed for a minimum of 10 minutes. The final pH of the solution was re-measured to ensure that the pH was within the range of 3.6 to 4.0 (target pH of 3.8). The compounded oral solution was filtered through a 0.2 μm filter into a suitable holding tank. The oral solution formulation density was 1112.3 mg/mL.

TABLE 2

Oral Solution Formulation components

| Component | Function | Quantity/unit (mg/mL) |
|---|---|---|
| palbociclib | API | 25.00 |
| DL Lactic Acid, 88.0-92.0% | Buffering system | 10.13 |
| Sodium Benzoate | Preservative | 1.00 |
| Xylitol | Sweetener | 320.00 |
| Sucralose | Sweetener | 8.00 |

TABLE 2-continued

Oral Solution Formulation components

| Component | Function | Quantity/unit (mg/mL) |
|---|---|---|
| Propyl Gallate | Antioxidant | 0.10 |
| Natural Grape Flavor WONF (Juicy Concord Type) (534732 T) | Flavor | 3.00 |
| Hydrochloric Acid | Buffering system, trace as needed | 0.005 |
| Water for Injection | Solvent | 550.00 |
| Water for Injection | Solvent | q.s. to 1 mL |

Example 3

Oral Solution Formulations Comprising Malic Acid

Oral solution formulations comprising malic acid were prepared essentially as described in Example 2. Formulation 3A (Table 3) comprises palbociclib at a solution concentration of 12.5 mg/mL. Formulation 3B (Table 4) comprises palbociclib at a solution concentration of 10 mg/mL.

TABLE 3

Oral Solution Formulation 3A components

| Component | Function | Theoretical Wt. (g) | Quantity/unit (mg/mL) |
|---|---|---|---|
| palbociclib | API | 2.50 | 12.50 |
| Malic Acid | Buffering system | 5.36 | 26.80 |
| Sodium Benzoate | Preservative | 0.30 | 1.50 |
| Xylitol | Sweetener | 20.00 | 100.00 |
| Sucralose | Sweetener | 0.20 | 1.00 |
| Propyl Gallate | Antioxidant | 0.20 | 1.00 |
| Grape Flavor WONF (3009672) | Flavor | 0.20 | 1.00 |
| Disodium EDTA | Antioxidant | 0.20 | 1.00 |
| Purified water | Solvent | q.s. 200 mL | |

TABLE 4

Formulation 3B components

| Component | Function | Theoretical Wt. (g) | Quantity/unit (mg/mL) |
|---|---|---|---|
| palbociclib | API | 0.25 | 10.00 |
| Malic Acid | Buffering system | 0.67 | 26.80 |
| Sodium Benzoate | Preservative | 0.0375 | 1.50 |
| Xylitol | Sweetener | 2.50 | 100.00 |
| Sucralose | Sweetener | 0.025 | 1.00 |
| Grape Flavor WONF (3009672) | Flavor | 0.025 | 1.00 |
| Disodium EDTA | Antioxidant | 0.025 | 1.00 |
| Purified water | Solvent | q.s. 25 mL | |

Example 4

Exemplary Powder for Constitution Formulations

Powder for constitution formulations were prepared by mixing each component in a bin blender and then filling the powder in bottles. The powder in bottle may be reconstituted with water to deliver the desired dose. Formulation 4A (Table 5) and Formulation 4B (Table 6) comprise malic acid as the buffer.

TABLE 5

Powder for constitution 4A components

| Component | Function | Theoretical Wt. (g) | Wt % |
|---|---|---|---|
| palbociclib | API | 8.93 | 8.93 |
| Malic Acid | Buffering system | 19.28 | 19.28 |
| Sodium Benzoate | Preservative | 1.07 | 1.07 |
| Xylitol | Sweetener | 69.30 | 69.30 |
| Sucralose | Sweetener | 0.71 | 0.71 |
| Grape Flavor WONF (3009672) | Flavor | 0.71 | 0.71 |
| Total | | 100.00 | |

TABLE 6

Powder for constitution 4B components

| Component | Function | Theoretical Wt. (g) | Wt % |
|---|---|---|---|
| palbociclib | API | 8.93 | 8.93 |
| Malic Acid | Buffering system | 19.28 | 19.28 |
| Sodium Benzoate | Preservative | 1.07 | 1.07 |
| Xylitol | Sweetener | 69.20 | 69.20 |
| Sucralose | Sweetener | 0.71 | 0.71 |
| Grape Flavor WONF (3009672) | Flavor | 0.71 | 0.71 |
| Disodium EDTA | Antioxidant | 0.10 | 0.10 |
| Total | | 100.00 | |

Example 5

Effect of Proton Pump Inhibitor on Relative Bioavailability of Palbociclib

A crossover, open label, non-randomized, pharmacokinetic (PK) study in healthy volunteers was conducted to estimate the effect of rabeprazole on the bioavailability of a single, 125 mg dose of palbociclib oral solution (OS) described in Table 7, prepared essentially as described in Example 2.

The palbociclib oral solution was tested in the presence and absence of rabeprazole under fasted conditions.

TABLE 7

Oral solution formulation for PK evaluation

| Component | Function | Quantity/unit (mg/mL) |
|---|---|---|
| palbociclib | API | 25.00 |
| DL Lactic Acid, 88.0-92.0% | Buffering system | 10.13 |
| Sodium Benzoate | Preservative | 1.50 |
| Xylitol | Sweetener | 100.00 |
| Sucralose | Sweetener | 1.00 |
| Propyl Gallate | Antioxidant | 1.00 |
| Natural Grape Flavor WONF (534732 T) | Flavor | 3.00 |
| Water for Injection | Solvent | q.s. to 1 mL |

The results provided in Table 8 demonstrated that the oral solution showed no drug-drug interaction with the proton-pump inhibitor, rabeprazole, under fasted conditions (Cmax and AUC).

TABLE 8

| Plasma Palbociclib Parameters [Units] | Adjusted Geometric Means | | Ratios | |
|---|---|---|---|---|
| | Palbociclib OS + Rabeprazole (Test) | Palbociclib OS Alone (Reference) | (Test/ Reference) of Adjusted Means | 90% CIs for Ratios |
| AUCinf [ng · hr/mL] | 1478 | 1451 | 101.83 | (93.67, 110.69) |
| Cmax [ng/ml] | 47.77 | 50.24 | 95.07 | (85.18, 106.11) |

The present invention may be embodied in other specific forms without departing from its spirit or essential characteristics.

The invention claimed is:

1. An oral aqueous solution comprising 6-acetyl-8-cyclopentyl-5-methyl-2-(5-piperazin-1-yl-pyridin-2-ylamino)-8H-pyrido[2,3-d]pyrimidin-7-one (palbociclib), or a lactate or malate salt thereof, and a buffer system comprising lactic acid or malic acid, wherein the palbociclib, or a lactate or malate salt thereof, is at a solution concentration of up to about 40.0 mq/mL.

2. The oral aqueous solution of claim 1, comprising palbociclib, or a lactate salt thereof, at a solution concentration of about mg/mL.

3. The oral aqueous solution of claim 1, wherein the buffer system comprises DL-lactic acid, D-lactic acid or L-lactic acid at a solution concentration of up to about 0.2M.

4. The oral aqueous solution of claim 3, wherein the buffer system comprises DL-lactic acid at a solution concentration of about 0.1M.

5. The oral aqueous solution of claim 1, comprising palbociclib, or a malate salt thereof, at a solution concentration of up to about 15.0 mg/mL.

6. The oral aqueous solution of claim 5, comprising palbociclib, or a malate salt thereof, at a solution concentration of about 12.5 mg/mL or about 10.0 mg/mL.

7. The oral aqueous solution of claim 5, wherein the buffer system comprises DL-malic acid, D-malic acid or L-malic acid at a solution concentration of about 0.2M.

8. The oral aqueous solution of claim 1, having a pH from about 3.6 to about 4.0.

9. The oral aqueous solution of claim 1, further comprising one or more pharmaceutically acceptable sweeteners selected from xylitol at a solution concentration from about 100.0 mg/mL to about 350.0 mg/mL and sucralose at a solution concentration from about 1.0 mg/mL to about 10.0 mg/mL, or mixtures thereof.

10. The oral aqueous solution of claim 1, wherein the solution further comprises one or more pharmaceutically acceptable flavorants.

11. The oral aqueous solution of claim 1, further comprising one or more pharmaceutically acceptable excipients selected from the group consisting of preservatives, antioxidants, pH adjusting agents, diluents, solubilizing agents, viscosity modifying agents and colorants.

12. The oral aqueous solution of claim 11, wherein the solution comprises one or more preservatives selected from benzoic acid and sodium benzoate, each at a solution concentration from about 1.0 mg/mL to about 1.5 mg/mL.

13. The oral aqueous solution of claim 11, wherein the solution comprises one or more antioxidants selected from propyl gallate and disodium EDTA, each at a solution concentration from about 0.1 mg/mL to about 1.0 mg/mL.

14. An oral aqueous solution comprising palbociclib at a solution concentration of about 25.0 mg/mL, lactic acid at a solution concentration of about 0.1M, xylitol at a solution concentration of about 320.0 mg/mL and sucralose at a solution concentration of about 8.0 mg/mL, said solution having a pH of from about 3.6 to about 4.0.

15. An oral aqueous solution comprising palbociclib at a solution concentration of about 12.5 mg/mL or about 10.0 mg/mL, malic acid at a solution concentration of about 0.2M, xylitol at a solution concentration of about 100.0 mg/mL and sucralose at a solution concentration of about 1.0 mg/mL, said solution having a pH of from about 3.6 to about 4.0.

16. The oral aqueous solution of claim 14, further comprising: (a) a pharmaceutically acceptable flavorant at a solution concentration from about 1.0 mg/mL to about 3.0 mg/mL; (b) sodium benzoate at a solution concentration of about 1.0 mg/mL to about 1.5 mg/mL; and/or (c) propyl gallate at a solution concentration of about 0.10 mg/mL to about 1.0 mg/mL.

17. The oral aqueous solution of claim 14, further comprising: (a) a pharmaceutically acceptable flavorant at a solution concentration of about 3.0 mg/mL; (b) sodium benzoate at a solution concentration of about 1.0 mg/mL; and (c) propyl gallate at a solution concentration of about 0.10 mg/mL.

18. The oral aqueous solution of claim 15, further comprising: (a) a pharmaceutically acceptable flavorant at a solution concentration from about 1.0 mg/mL to about 3.0 mg/mL; (b) sodium benzoate at a solution concentration of about 1.0 mg/mL to about 1.5 mg/mL; and/or (c) propyl gallate at a solution concentration of about 0.10 mg/mL to about 1.0 mg/mL.

* * * * *

UNITED STATES PATENT AND TRADEMARK OFFICE
CERTIFICATE OF CORRECTION

PATENT NO. : 11,911,383 B2
APPLICATION NO. : 17/055102
DATED : February 27, 2024
INVENTOR(S) : Ashwinkumar Jain et al.

It is certified that error appears in the above-identified patent and that said Letters Patent is hereby corrected as shown below:

In the Claims

At Column 15, Line 25, Claim 1, "40.0 mq/mL" should be --40.0 mg/mL--.

At Column 15, Line 28, Claim 2, "mg/mL" should be --25.0 mg/mL--.

Signed and Sealed this
Fifteenth Day of October, 2024

Katherine Kelly Vidal
*Director of the United States Patent and Trademark Office*